(12) United States Patent
Brooke

(10) Patent No.: US 11,419,663 B2
(45) Date of Patent: Aug. 23, 2022

(54) ELECTROSURGICAL INSTRUMENTS

(71) Applicant: Gerard Brooke, Gloucestershire (GB)

(72) Inventor: Gerard Brooke, Gloucestershire (GB)

( * ) Notice: Subject to any disclaimer, the term of this patent is extended or adjusted under 35 U.S.C. 154(b) by 763 days.

(21) Appl. No.: 15/300,776

(22) PCT Filed: Mar. 30, 2015

(86) PCT No.: PCT/GB2015/050971
§ 371 (c)(1),
(2) Date: Sep. 29, 2016

(87) PCT Pub. No.: WO2015/150769
PCT Pub. Date: Oct. 8, 2015

(65) Prior Publication Data
US 2017/0020599 A1 Jan. 26, 2017

(30) Foreign Application Priority Data
Mar. 31, 2014 (GB) .................................... 1405745

(51) Int. Cl.
A61B 18/14 (2006.01)
A61B 18/00 (2006.01)
A61B 17/00 (2006.01)

(52) U.S. Cl.
CPC ...... *A61B 18/1402* (2013.01); *A61B 18/1442* (2013.01); *A61B 2017/00424* (2013.01);
(Continued)

(58) Field of Classification Search
CPC .... A61B 2218/008; A61B 2018/00916; A61B 2017/32007; A61B 2218/006;
(Continued)

(56) References Cited

U.S. PATENT DOCUMENTS 3,911,241 A * 10/1975 Jarrard ............... A61B 18/1402
200/517
5,071,418 A 12/1991 Rosenbaum
(Continued)

FOREIGN PATENT DOCUMENTS

| CA | 2488877 A1 | 6/2006 |
|---|---|---|
| WO | 2005046498 A1 | 5/2005 |
| WO | 2013175463 A2 | 11/2013 |

OTHER PUBLICATIONS

International Preliminary Report on Patentability of PCT Patent Application No. PCT/GB2015/050971 dated Oct. 4, 2016.
(Continued)

*Primary Examiner* — Eun Hwa Kim
*Assistant Examiner* — Catherine Premraj

(57) ABSTRACT

An electrosurgical instrument (1) is disclosed including a housing (2) comprising an elongate main body (3), extending in an axial direction and a grippable member (12). An implement (4) is fixed relative to and projecting from a forward region of the main body (3). A smoke evacuation passage (8) is defined within the main body (3) and extends from an inlet proximal to the implement (4). An electrical conductor (11) is housed within the housing (2) for supplying an electro-surgical current to the implement (4). The grippable member (12) is slidably connected to the main body (3) such that the axial position of the grippable member (12) relative to the main body (3) may be adjusted in use. Further there is provided a controllable smoke passage obstructor (25) for enabling adjustment of the throughput of the smoke passing through the interior of the housing (2).

15 Claims, 7 Drawing Sheets

(52) U.S. Cl.
CPC ............ *A61B 2018/00196* (2013.01); *A61B 2018/00589* (2013.01); *A61B 2018/00601* (2013.01); *A61B 2018/00607* (2013.01); *A61B 2018/00916* (2013.01); *A61B 2018/1412* (2013.01); *A61B 2218/008* (2013.01)

(58) Field of Classification Search
CPC ........ A61B 2218/007; A61B 2218/001; A61B 18/1402; A61B 18/1442; A61B 2017/00424; A61B 2018/00196; A61B 2018/00589; A61B 2018/00601; A61B 2018/00607; A61B 2018/1412
See application file for complete search history.

(56) References Cited

U.S. PATENT DOCUMENTS

| | | | | |
|---|---|---|---|---|
| 5,312,400 A | * | 5/1994 | Bales | A61B 17/3203 606/41 |
| 6,099,525 A | * | 8/2000 | Cosmescu | A61B 18/00 604/35 |
| 2004/0030330 A1 | * | 2/2004 | Brassell | A61B 18/1206 606/41 |
| 2004/0092927 A1 | * | 5/2004 | Podhajsky | A61B 18/1402 606/42 |
| 2008/0299517 A1 | * | 12/2008 | Delaney, II | A61C 13/245 433/185 |
| 2009/0248018 A1 | * | 10/2009 | Kerr | A61B 18/1477 606/42 |
| 2014/0052131 A1 | * | 2/2014 | Busch-Madsen | A61B 18/1477 606/41 |

OTHER PUBLICATIONS

Search Report of counterpart British Patent Application No. 1405745.9 dated Oct. 10, 2014.

* cited by examiner

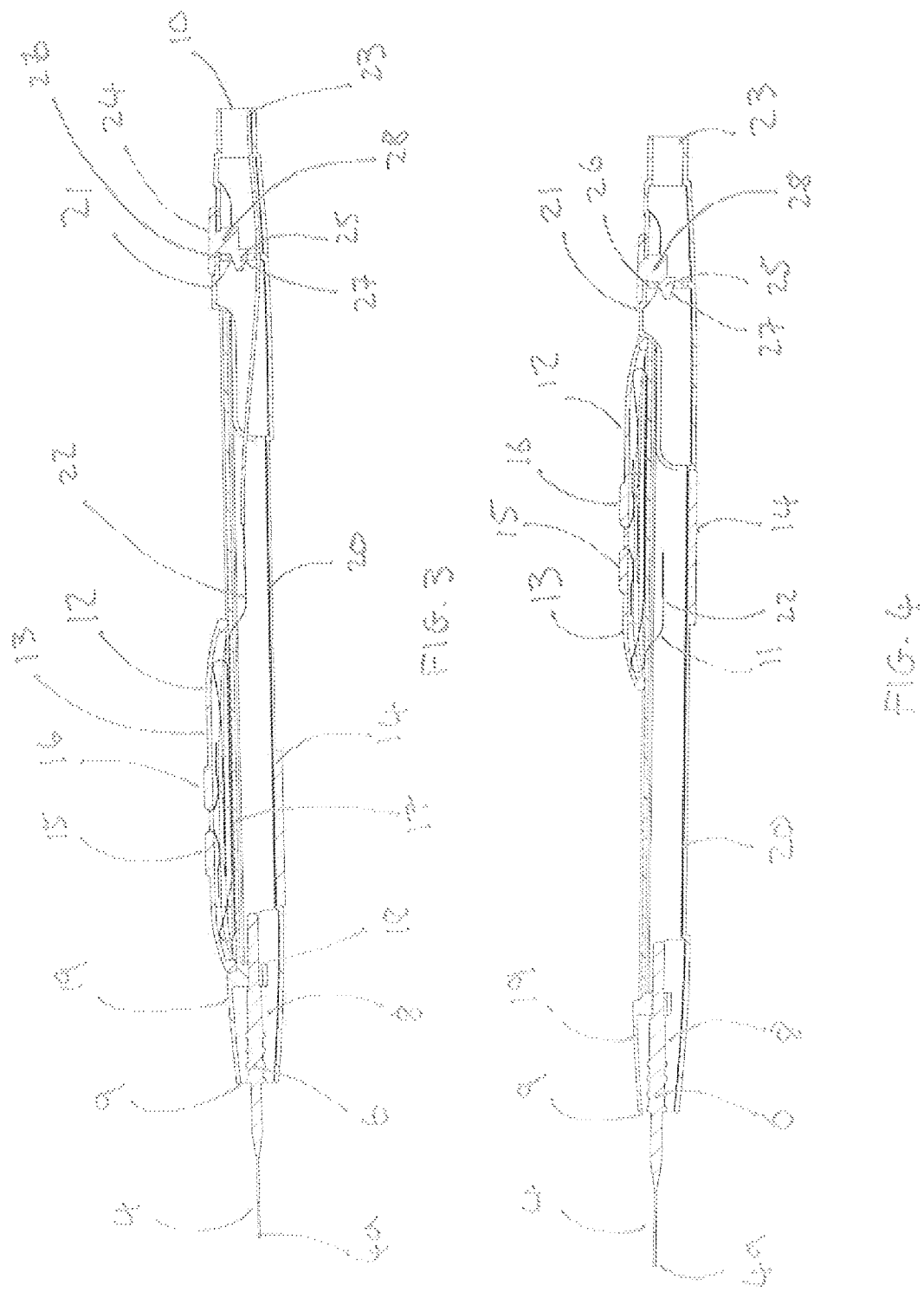

ELECTROSURGICAL INSTRUMENTS

FIELD OF THE INVENTION

This invention relates to an electrosurgical instrument, in particular for use at different depths within a patients' body.

BACKGROUND OF THE INVENTION

Electrosurgical instruments normally comprise a main body portion which is held by the surgeon and which contains electro-surgical power supply, and an electro-surgical implement projecting from the forward end thereof to which the electro-surgical current is applied by power supply. The power supply may include some control circuitry or may be a power line which is arranged to be connected to a remotely located control circuitry in use (and may for example be controlled using a foot pedal).

Such instruments are typically selectively operable to effect cutting or coagulation of tissue by the application of high frequency current via the electro-surgical implement which acts as an electrode.

In some applications the instrument may be required to be used in different applications, relating to different depths within a patient's body. One way of providing such an arrangement is to provide an arrangement which enable the position of the tip of the electrode to be variable with respect to the rearward end of the main housing.

For example, U.S. Pat. No. 7,935,109 describes a telescopic surgical device, whereby the electrode length can be adjusted via a telescopic means. The first end and the second end of the main body are in continuous communication and the movement is provided by a moveable telescopic body circumferentially contained within at least part of the main body. The electrode itself is contained within at least a portion of the telescopic body: therefore movement of the telescopic body provides movement of the electrode whereby the tip of the electrode is moved away from the first end and the second end of the main body. Whilst this provides the desired extension for implementation of the electrode at regions positioned deeper within a patients' body, the extension of the tip from the forward end of the main body creates less control of the tip of the electrode by the surgeon holding the main body. This could cause contact of the tip being made at undesired regions within the patients' body.

Such a device also includes a smoke evacuation means coupled to the end of the main body portion for removing smoke and debris produced during the medical procedure, so as to minimise the health risk of the smoke to the surgeon or others in the vicinity of the smoke. It is common for a constant throughput of the smoke to be use. This constant throughput may not be desirable in applications where less smoke is provided and therefore less of an extraction effect is required.

Embodiments of the present invention are derived from the realisation that there exists a need to provide an alternative telescopic electro-surgical device that optimises the surgeon's control of the tip of the electrode. There is also the need for controlling the smoke evacuation at the rear of the device.

SUMMARY OF THE INVENTION

According to a first aspect of the present invention, there is provided an electrosurgical instrument including:

a housing comprising an elongate main body, extending in an axial direction, and a grippable member;

an implement fixed relative to and projecting from a forward region of the main body;

a smoke evacuation passage defined within the main body and extending from an inlet proximal to said implement;

an electrical conductor housed within the housing for supplying an electro-surgical current to the implement;

the grippable member being slidable connected to the main body such that the axial position of the grippable member relative to the main body may be adjusted in use.

In use the rearward portion of the smoke evacuation passage may be connected to an evacuation means, which encourages the smoke and/or fumes produced proximal to the implement to pass through the interior of the housing through the smoke evacuation passage.

The grippable member is a member of the electrosurgical instrument that may be arranged to be grasped between the fingers of the user during use. This provides an ergonomic arrangement enabling ease of use.

The implement may be an electrode.

Preferably, the grippable member may be moveable between a rearwardmost position whereby the rearward end of the grippable member is spaced apart from the rear portion of the housing and a forwardmost position whereby the front end of the grippable member is spaced apart from the front portion of the housing.

The grippable member and the housing may be provided with complementary engagement formations. The complementary engagement features may resiliently engage. The resilient engagement may hold the grippable member in position during normal use and require a relatively high force to be applied by the user to adjust the position relative to the housing (in order to overcome the resilient engagement). The grippable member and the housing may be provided with complementary engagement formations.

The complementary engagement formations may provide indexed positions for the grippable member along the longitudinal axis of the housing.

The indexing positions may be provided by a rack on at least one side of the housing and a complementary profiled tooth on the grippable member. The tooth may for example be an inwardly projecting tooth on an inner surface of the grippable member. The rack may be provided on an outer surface of the housing and may, for example, extend in the axial direction.

The grippable member may be a carriage which may be moveable along the longitudinal axis of the housing. For example, the grippable member may at least partially surround the housing. The grippable member may, for example, include a substantially annular portion.

The electrical conductor may be provided to energise the electrode whereby the electrical conductor is positioned on the surface of a flexible membrane. For example, the flexible membrane may comprise a thin insulating polymer film having conductive circuit patterns applied thereto and may further include a thin polymer coating to protect the circuitry).

When the grippable member is in the rearwardmost position the flexible membrane may be foldable.

The grippable member may include at least one switch for activating the electrosurgical instrument. The switch may be a membrane switch formed on flexible circuit. The switch may be positioned under a resiliently moveable button formed on the grippable member.

In a further embodiment of the invention, the electrosurgical instrument may include a controllable smoke pathway obstructor for enabling adjustment of the throughput of the smoke passing through the interior of the housing.

The obstructor may be attached to a slideable actuator located at the surface of the main part of the housing.

The obstructor may be positioned within the housing and may be arranged to be used in conjunction with an aperture also positioned within the the housing. The aperture may be defined within the smoke evacuation passage.

The obstructor may be moveable between a first position maximising the throughput through the aperture and a second position minimising the throughput through the aperture. In the first position the aperture may be substantially unobstructed by the obstructor. In the second position the aperture may be at least partially obstructed by the obstructor. In the second position part of the aperture may remain unobstructed by the obstructor.

Preferably, the obstructor is a bung, wherein the bung has a conical shaped leading end. The shape of bung may be complementary with a portion of the aperture. For example, the aperture may be substantially "T"-shaped and the bung may be received by the aperture at the region where the horizontal and vertical parts of the "T"-shape merge.

According to a second aspect of the invention there is provided an electrosurgical instrument including:

a grippable housing defining a smoke evacuation passage passing there-through;

an implement extending from the housing, in use, and proximal to an inlet of the smoke evacuation passage;

an outlet of the smoke evacuation passage arranged to be connected, in use, to a smoke evacuation device for removing smoke and/or fumes produced during a medical procedure using the implement; and a controllable smoke passage obstructor for enabling adjustment of the throughput of the smoke passing through the interior of the grippable housing.

The implement extending from the housing, in use, could be fixed or moveable.

The outlet of the smoke evacuation passage is typically located at the rearward end of housing and the smoke evacuation device may be connected via a flexible tubing.

The obstructor may be attached to a slideable actuator located at the surface of the housing. The obstructor may be axially slidable along the longitudinal axis of the grippable housing.

The obstructor may be positioned within the housing and may be arranged to be used in conjunction with an aperture also positioned within the the housing. The aperture may be defined within the smoke evacuation passage.

The obstructor may be moveable between a first position maximising the throughput through the aperture and a second position minimising the throughput through the aperture. In the first position the aperture may be substantially unobstructed by the obstructor. In the second position the aperture may be at least partially obstructed by the obstructor.

In the second position part of the aperture may remain unobstructed by the obstructor.

Preferably, the obstructor is a bung which may be resiliently held in position by the interface between housing and actuator. For example the actuator may resiliently engage the housing.

The bung has a conical shaped leading end, wherein the shape of the bung may be complementary with a portion of the aperture.

For example, the aperture is substantially "T"-shaped and the bung is received at the region where the horizontal and vertical parts of the "T"-shape merge. The implement may be an electrode.

Whilst the invention has been described above, it extends to any inventive combination of features set out above or in the following description or drawings.

BRIEF DESCRIPTION OF THE DRAWINGS

A specific embodiment of the invention will now be described in detail, by way of example only, and with reference with the accompanying drawings in which:

FIG. 3 is a schematic cross-section of the electrosurgical instrument in the retracted state;

FIG. 4 is a schematic cross-section of the electrosurgical instrument in the extended state;

Figure 1:
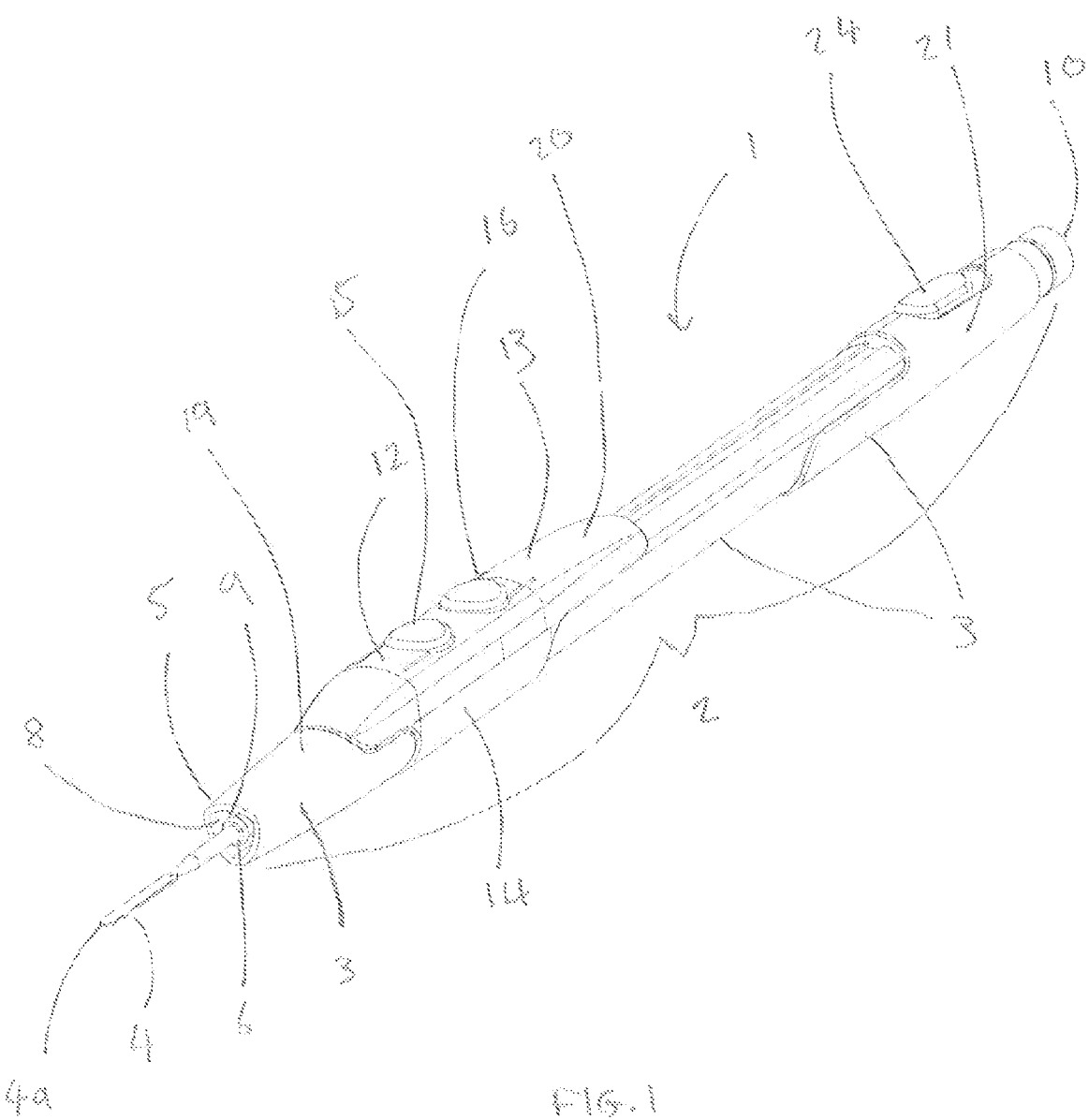
FIG. 1 is a perspective view of the electrosurgical device in a retracted configuration.
Figure 2:
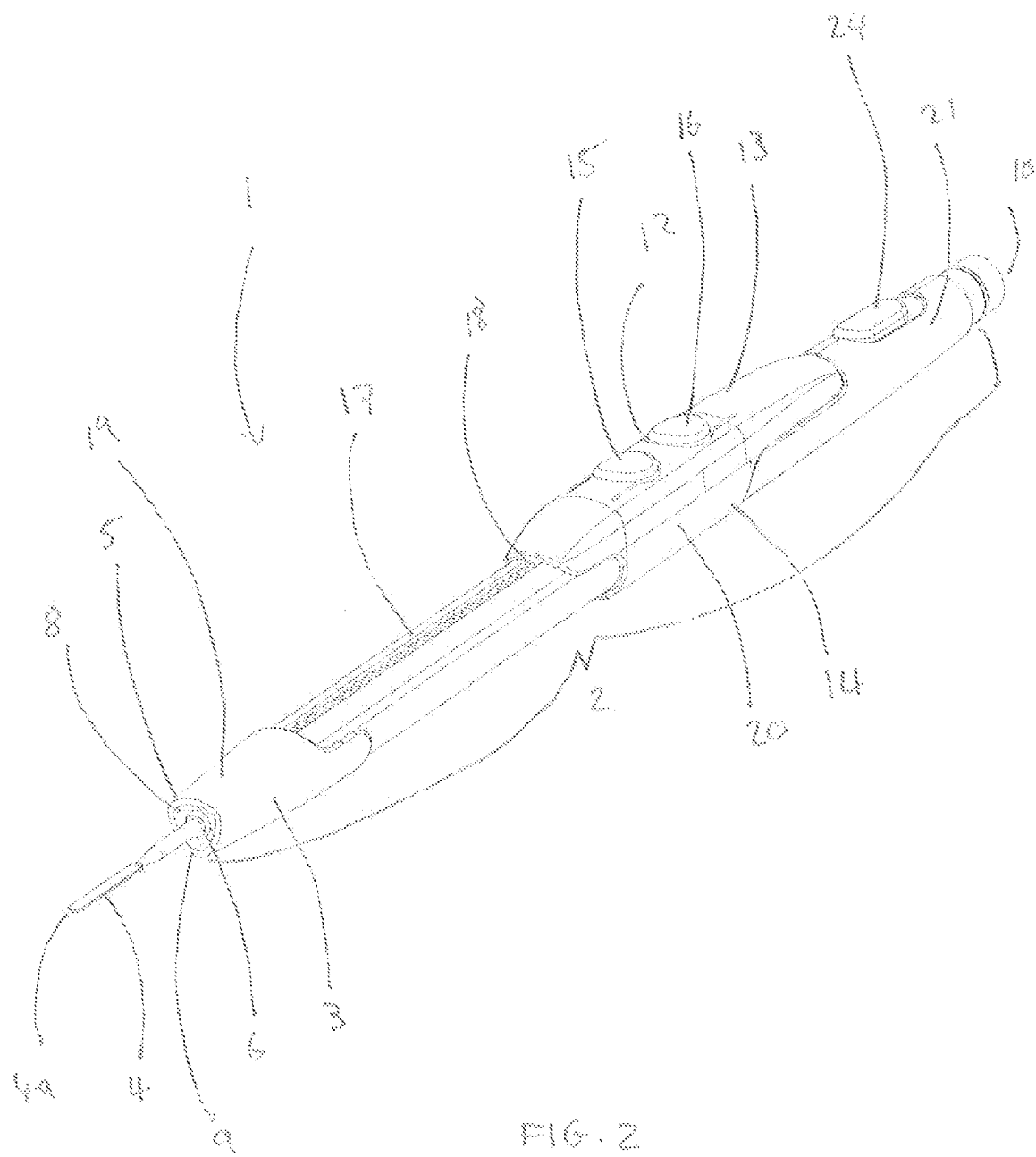
FIG. 2 is a perspective view of the electrosurgical instrument in an extended configuration.

Referring firstly to FIG. 1 and FIG. 2, there is shown an electrosurgical instrument 1 including a housing 2 comprising an elongate main body 3 extending in an axial direction. An implement 4 for electrosurgery is provided at a forward end of the instrument 1 (it will be appreciated that references to forward as used herein refer to the direction towards the end of the instrument which is intended to be directed towards the patient in use; likewise rearward will be understood to be the direction away from the patient). The implement 4 is fixed relative to and projecting from a forward region 5 of a main body 3 is included as best seen in the cross section of FIGS. 3 and 4, the implement 1 is rigidly attached to a mounting feature 6 within the interior of the housing, positioned rearward of the forward edge of the housing.

The main body 3 is a generally circular tubular body having a central bore 8 extending there-through. As such, a smoke evacuation passage is defined within the main body 3 and is used to remove the smoke and/or fumes produced during the medical procedure. The smoke evacuation passage 8 extends from an inlet 9 proximal to said implement to an outlet 10 at the rearward end of the housing 2. The inlet 9 generally surrounds the implement 4 and has an annular cross section. The outlet 10 at the rear of the housing 2 is arranged to be connected in use to a flexible tubing (not shown) through which a suction vacuum may be provided. The housing 2 further contains an electrical conductor 11 for supplying an electro-surgical current to the implement 4.

A grippable member 12 is slideably connected to the main body 3 such that the axial position of the grippable member 12 relative to the main body 3 may be adjusted in use. The grippable member 12 includes an upper portion 13 which is intended to be held by the forefinger of a surgeon in use (in a "pen like" grip). The grippable member 12 also includes a lower portion 14 which extends around the opposing surface of the housing 2 and retains the member thereon.

A first and second switch or button 15, 16 is located on the surface of the upper portion 13 of the grippable member 12 and is for activating the electrosurgical instrument to coagulate or cut respectively. The first and second switch or button 15, 16 are to be operated by the surgeon, in use.

FIG. 2 shows that the grippable member 12 and the main body 3 are provided with complementary engagement formations whereby the complementary engagement formations provide indexed positions for the grippable member 12 along the longitudinal axis of the main body 3 of the housing (along it's middle portion).

The indexing positions are provided by a track 17 on at least one side of the main part 3 of the housing 2 and a complementary profiled tooth 18 located on the grippable member 12. The tooth 18 is formed by a radially inwardly directed projection extending from the forward lower end of the grippable member 12.

The grippable member 12 is a carriage which is moveable along the longitudinal axis of the main body 3 of the housing 2. On application of a sufficient force the carriage is slidable against the retention of the track 17 and the tooth 18. The grippable member 12 may for example "click" along the track by resilient deformation of the track 17 and/or tooth 18. This may provide a tactile and/or audible indexing of the position. The main body 3 of the housing 2 is formed of a front portion 19, a middle portion 20, along which the grippable member 12 is moveable and a rear portion 21. The grippable member 12 is moveable between a rearwardmost position whereby the rearward end of the grippable member 12 is spaced apart from a rear portion 21 of the housing and a forwardmost position whereby the forward end of the grippable member 12 is spaced apart from a front portion 19 of the housing 2.

Whilst the grippable member can move between the forwardmost and rearwardmost positions, it may also be arranged at discrete intervals there-between.

An evacuation means (not shown) is couplable to a rearward portion of the smoke evacuation passage that encourages smoke and/or fumes produced proximal to the implement or electrode 4 to pass through the interior of the main body 3 of the housing 2 along the passage 8 towards the rearward end of the evacuation passage 8. Therefore, the smoke or fumes are removed from the site of the medical procedure. The evacuation means applies a vacuum to the rearward end of the passage 8.

Whilst it is particularly desirable to remove smoke or fumes during a medical procedure, other debris can also extracted via the tube. An actuator, for example a switch, is provided on the rear portion of the elongate main body 3 of the housing 2 for varying the through-put of smoke or fumes along the passage defined within the main body 3.

In use a user grasps the grippable member 12 between the fingers of the user and applies a force along a longitudinal direction of choice, dependent on the desired application of use. The user thereby selects a desired position of the grippable member 12 between a forwardmost position, whereby the distance between the electrode tip 4a and the forward region of the grippable member 12 is minimised as shown in FIG. 1 and a rearwardmost wherein the distance between the tip 4a of the electrode 4 and the front end of the grippable member 12 is minimised as shown in FIG. 2. This movement is performed along the middle portion 20 of the main body 3 and between the front portion 19 and the rear portion 21 of the main body 3. The front portion and the rear portion effectively act as stops as the grippable portion 12 is brought into is forwardmost and rearwardmost position respectively.

In both the forwardmost position and the rearwardmost position the relative distance between the tip 4a of the electrode 4 and the front portion 19 of the main body 3 of the housing 2 is maintained as shown in FIG. 1 and FIG. 2. However, the relative distance between the tip 4a of the electrode 4 and the forward end of the grippable member 12 is variable.

In use when in the grippable member 12 is in the forwardmost state the users instrument gripping hand is positioned close to the electrode 4. When the grippable member 12 is in the rearwardmost state the users gripping hand is spaced apart from the electrode 4, enabling the electrode 4 to be positioned deeper within the patient without the surgeons' hand causing an obstruction. Therefore, the grippable member 12 is moveable so as to enable the adjustment of the distance between the electrode tip 4a and the surgeons' gripping hand.

Clearly it is important for the electrode 4 to be connected to an energy source (not shown) with an energy transferring means (i.e. an electrical conductor 11) being arranged to transfer the energy from the energy source to the electrode in the form of a current. Electronic drive circuitry transfers the power to the electrode and controls the output at the electrode 4 and comprises the electrical conductor 11 in the form of a current carrying pathway and a first and second switch 15, 16 enabling switching between a continuous sinusoidal signal for the cutting function and a modulated sinusoidal signal for the coagulating function. To enable relative movement of the grippable member 12 and the main body 3 of the housing 2 the electrical conductor is positioned on the surface of a flexible membrane 22. The flexible membrane 22 comprise a thin insulating polymer film having conductive circuit patterns applied thereto and having a thin polymer coating to protect the circuitry. Part of the flexible membrane 22 is contained within the interior of the main body 3 of the housing 2, whereas the other part of the flexible membrane 22 is positioned exterior to the main part of the housing 3, but contained within the grippable member 12 of the housing 2. This ensures a good electrical connection is maintained in both the forwardmost and rearwardmost positions as shown in FIGS. 3 and 4 respectively. Advantageously, utilising a flexible membrane 22 with the electrical conductor 11 positioned thereon enables the movement of the grippable member 12 to be accommodated whilst also allowing the switching and control functions to be provided within the instrument 1. This, for example, enables embodiments of the invention to provide a user-friendly finger switch type device with the possibility of a variable depth of operation. In FIG. 4 the flexible membrane 22 is folded whilst ensuring that there is no shorting of the electrical conductor 11. This is achieved by the first and second overlapping parts of the flexible circuit membrane 22 being separated by an external wall of the main body 3 of the housing 2.

The first and second switches 15, 16 located on the upper portion of the grippable member 12 are arranged to engage a membrane switch (not shown) which is located on the circuit membrane 22.

In use, the electrode 4 of the electrosurgical instrument creates smoke that can be a health hazard to the surgeon and other people in the vicinity of the smoke and may be considered toxic or unpleasant. Therefore, a smoke evacuation means is activated which causes the smoke at the electrode 4 to be drawn through the interior of the main body 3 via the bore 8 and out through a smoke evacuation port located at the rear of the main body 3 of the housing 2.

Figure 5:
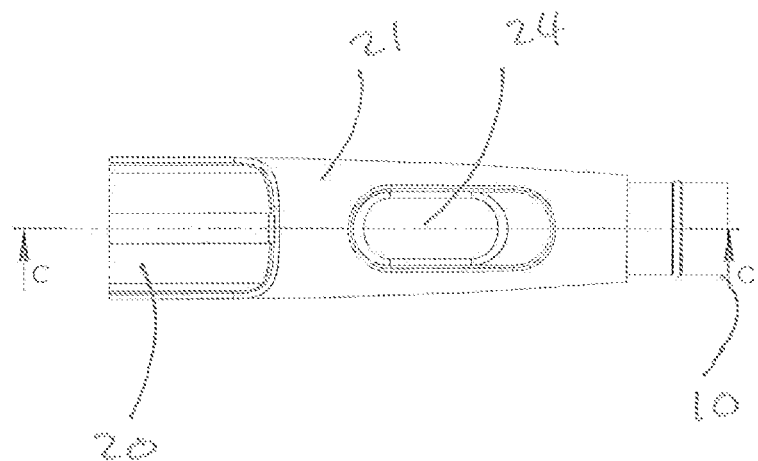
FIG. 5 is a top view of part of the electrosurgical device with the switch in a closed state.

A slideable actuator 24 is located at the upper surface of the main body 3 of the housing, as shown in FIG. 5. The slideable actuator 24 is in mechanical communication with a controllable smoke passage obstructor 25, as shown in FIGS. 6 and 7 for enabling adjustment of the through-put of the smoke passing through the smoke passage 8 which is located within the main body 3 of the housing 2.

The obstructor 25 is positioned within the main body of the housing within the bore 8 and is arranged to be used in conjunction with a wall 26 and aperture 27 arrangement also positioned within the main body 3 of the housing 2 at the rear portion 21. Therefore, the aperture 27 is defined within the smoke evacuation passage 8. The actuator 24 is generally radially offset from the obstructor 25 and is connected thereto by a radially extending arm 28. The obstructor 25 is centrally located within the bore 8 of the housing 2.

Figure 6:
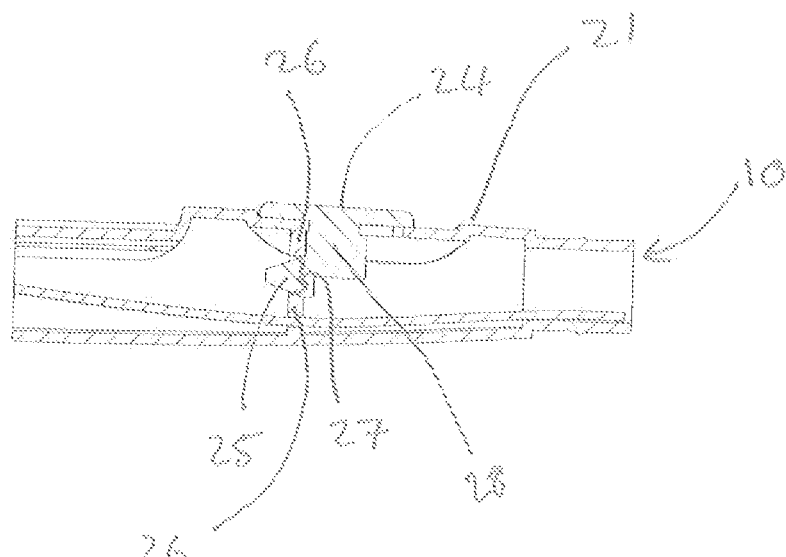
FIG. 6 is a cross section through C-C of FIG. 5.
Figure 7:
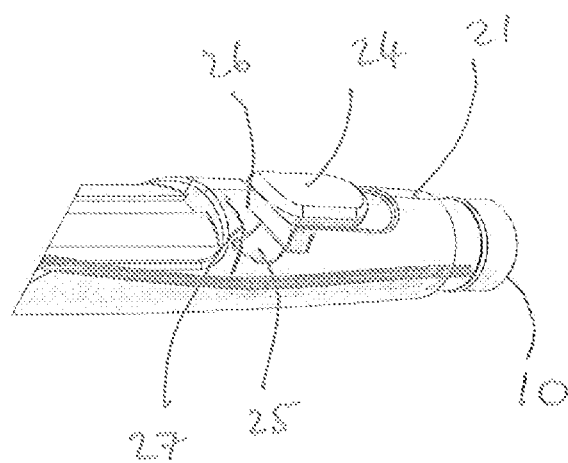
FIG. 7 is a part transparent perspective view of the end of the electrosurgical device in FIG. 6.
Figure 8:
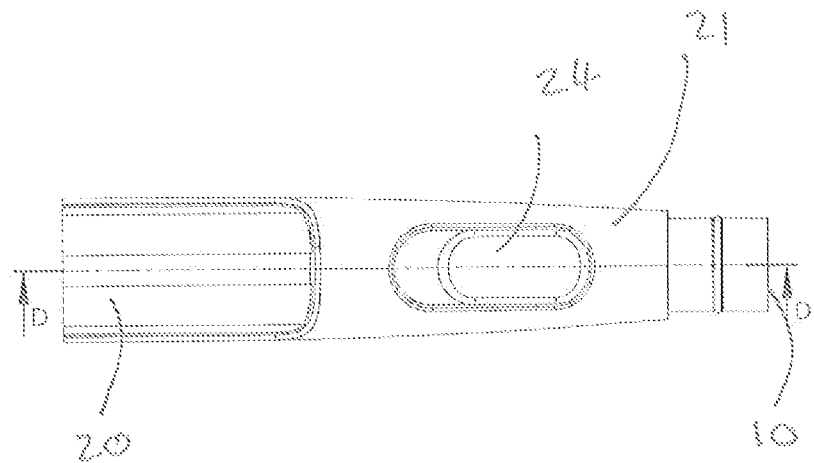
FIG. 8 is a top view of part of the electrosurgical device with the switch in an open state.
Figure 9:
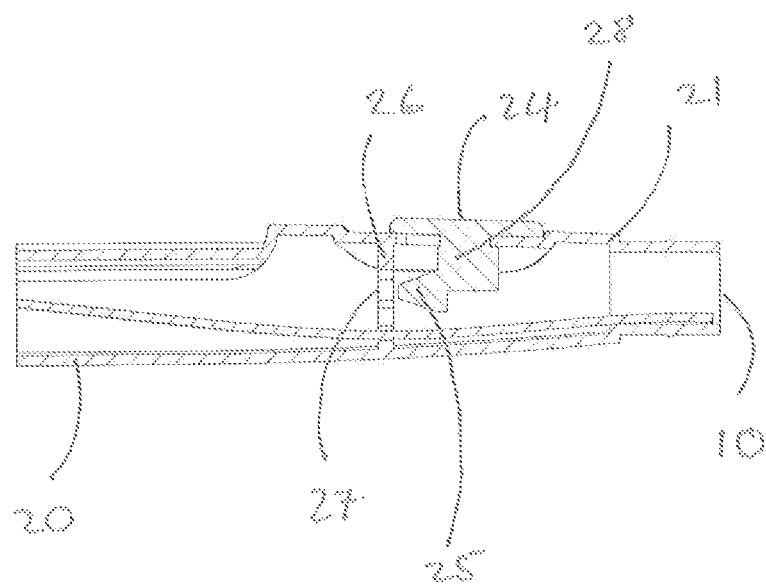
FIG. 9 is a cross section through D-D of FIG. 8.
Figure 10:
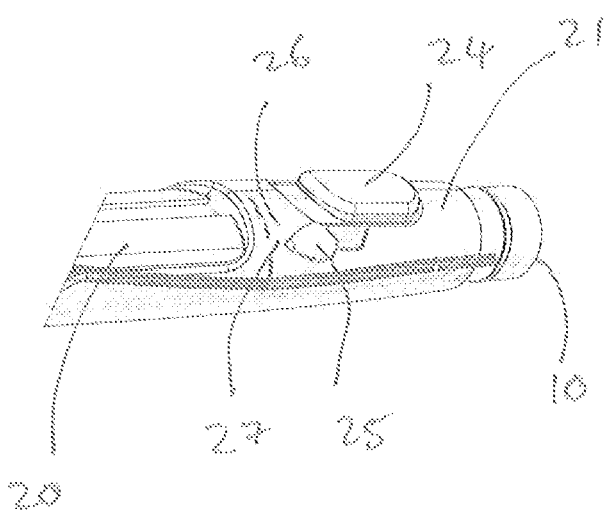
FIG. 10 is a part transparent perspective view of the end of the electrosurgical device in FIG. 9.

The slideable actuator 24 is moveable between an open and closed state, shown in FIGS. 5 and 8 respectively, causing movement of the obstructor 25 between a first position maximising the throughput through the aperture 27 (as shown in FIGS. 9 and 10) and a second position minimising the throughput through the aperture 27 (as shown in FIGS. 6 and 7) respectively. In the first position the aperture is substantially unobstructed whereas in the second position the aperture 27 is at least partially obstructed by the obstructor 25.

In the closed state of the actuator 24, corresponding to the second position of the obstructor 25, part of the aperture 27 remains unobstructed by the obstructor 25 such that some smoke is still permitted to pass there-through, all-be-it through a minimised area.

The obstructor 25 is a bung having a conical shaped leading end. The shape of bung 25 is complementary with a portion of the aperture 27, but does not cause the blockage of the entire aperture 27. The bung is formed of rubber.

FIGS. 7 and 10 show the aperture 27 to be substantially "T"-shaped and the bung 25 being received by the aperture 27 at the region where the horizontal and vertical parts of the "T"-shape merge. Alternatively, an aperture 27 with at least one radial arm extending therefrom may be used. For example there could be provided a substantially "I" shaped aperture. The obstructor 25 may be arranged to obstruct the central opening of the aperture 27 but at most only partially obstruct the radially extending arm portion.

In an alternative embodiment of the invention there is provided an electrosurgical instrument 1 having a grippable housing 12 defining a smoke evacuation passage 8 passing there-through. An implement 4, for example an electrode 4, extends from the housing 2, in use, and is proximal to an inlet 9 of the smoke evacuation passage. The outlet 10 of the smoke evacuation passage 8 is arranged to be connected to a smoke evacuation device (not shown) which is coupled to the grippable housing 12 for removing smoke and/or fumes produced during a medical procedure using the implement 1. To control the flow of smoke through the passage 8 of the instrument 1 a controllable smoke passage obstructor 25 is provided for enabling adjustment of the throughput of the smoke passing through the interior of the grippable housing 12. The smoke evacuation device creates a vacuum source. Therefore, the use of the obstructor 25 allows the restriction of vacuum extraction or exhaust of smoke i.e. allows the vacuum to be reduced but does not block the aperture 27 completely. The shape of the bung 25 and the aperture 27 are therefore designed and manufactured not to be matched. The obstructor 25 is a bung having a conical leading end that aids insertion of the bung into part of the aperture. The actuator for the bung 25 is formed of a slideable button that enables the bung 25 to be moved reciprocally linearly along the longitudinal axis of the grippable housing 12 so as to minimise and maximise the through-put of smoke through the interior of the housing 2 and towards the outlet 10 of the passage. Intermediate states between open and close may be attained.

While the invention has been described above with reference to a preferred embodiment, it will be appreciated that various changes or modifications may be made without departing from the scope of the invention as defined in the appended claims. For example, the bung may be arranged to block the ends of the arms of the aperture and for the central merging point to remain unobstructed. Therefore, the shape of the bung 25 may take another form and may be made from any suitable materials, for example plastics or composite. The bung assembly may be of a more complicated form, for example the bung 25 may take an arcuate path so that in the open state, the bung is not aligned with the aperture 27. Rather than the provision of a bore 8 there-through, the main part of the housing may be hollow.

The aperture 27 to be used with the bung 25 may take many different shapes, with the central aperture having at least one arm. In the closed state the bung 25 will block the central aperture, but the arms of the aperture may remain unobstructed. The aperture 27 may take another form, for example a central aperture with concentric ring, whereby the central aperture may be blocked, but the concentric rings are unobstructed.

Another implement may be used other than an electrode 4, for example forceps.

The power lead supply electricity to the instrument 1 may be hard wired, or may instead be detachable, e.g. a plug and socket type arrangement.

The electronic conductor may be a wire or a circuit applied to the membrane. Considering the flexible circuits, many different types of flexible circuits exist including one metal layer, double sided, multilayer and rigid flex circuits. Alternatively, flexible circuit assemblies may be implement whereby the printed or etched circuits include electrical components.

Alternatively to the aperture 27 and bung 25 described above, the bung may be arranged to block the aperture in its entirety in the closed state so as to block the passage of the smoke through the interior of the housing. This can be achieved by, for example, the bung being the same shape as the aperture and it being fully co-operable therewith.

The invention claimed is:
1. An electrosurgical instrument including:
a housing comprising an elongate main body, extending in an axial direction, and a grippable member, wherein the elongate main body has a front portion, a rear portion, and a middle portion between the front and rear portions; an implement fixed relative to and projecting from a forward region of the elongate main body; a smoke evacuation passage defined within the elongate main body and extending from an inlet proximal to said implement; an electrical conductor which supplies an electro-surgical current to the implement; and wherein the grippable member is a slidable carriage having an upper portion extending longitudinally along an outer surface of the housing and a lower portion extending circumferentially around the outer surface of the housing, the grippable member being moveable along the middle portion of the housing along a longitudinal axis thereof; further comprising a switch on the upper portion of the grippable member configured to activate at least one function of the electrosurgical implement;

wherein a first part of the electrical conductor is contained within the elongate main body of the housing, and a second part of the electrical conductor is contained within the grippable member to accommodate the movement of the grippable member whilst also allowing the at least one function to be activated by the switch.

2. An electrosurgical instrument according to claim 1, wherein the implement is an electrode.

3. An electrosurgical instrument according to claim 1, wherein the grippable member is moveable between a rearwardmost position whereby the rearward end of the grippable member is spaced apart from a rear portion of the housing and a forwardmost position whereby the forward end of the grippable member is spaced apart from a front portion of the housing.

4. An electrosurgical instrument according to claim 1, wherein the grippable member and the housing are provided with complementary engagement formations, wherein the complementary engagement formations provide indexed positions for the grippable member along the longitudinal axis of the housing, and wherein the indexing positions are provided by a rack on at least one side of the housing and a complementary profiled tooth on the grippable member.

5. An electrosurgical instrument according to claim 1, wherein the electrical conductor is provided to energize the electrode whereby the electrical conductor is positioned on a surface of a flexible membrane, wherein when the grippable member is in a rearwardmost position the flexible membrane is foldable.

6. An electrosurgical instrument according to claim 1, further including a controllable smoke passage obstructor which enables adjustment of a throughput of smoke passing through an interior of the housing along the smoke evacuation passage, wherein the controllable smoke passage obstructor is attached to a slidable actuator located at a surface of the housing, wherein the controllable smoke passage obstructor is positioned within the housing and is arranged to be used in conjunction with an aperture also positioned within the housing, wherein the aperture is defined within the smoke evacuation passage.

7. An electrosurgical instrument according to claim 6, wherein the controllable smoke passage obstructor is moveable between a first position maximizing the throughput through the aperture and a second position minimizing the throughput through the aperture, or wherein the controllable smoke passage obstructor is moveable between a first position whereby the aperture is substantially unobstructed by the controllable smoke passage obstructor and a second position whereby the aperture is at least partially obstructed by the controllable smoke passage obstructor.

8. An electrosurgical instrument according to claim 7, wherein in the second position part of the aperture remains unobstructed by the controllable smoke passage obstructor.

9. An electrosurgical instrument according to claim 7, wherein the controllable smoke passage obstructor is a bung having a conical shaped leading end, the shape of the bung being complementary with a portion of the aperture.

10. An electrosurgical instrument according to claim 9, wherein the aperture is substantially "T"-shaped and the bung is received by the aperture at a region where the horizontal and vertical parts of the "T"-shape merge.

11. An electrosurgical instrument according to claim 5, wherein the flexible membrane comprises a thin insulating polymer film having conductive circuit patterns applied thereto.

12. An electrosurgical instrument according to claim 11, wherein the flexible membrane includes a thin polymer coating to protect the conductive circuit patterns.

13. An electrosurgical instrument according to claim 5, wherein, in a folded condition of the flexible membrane, a first overlapping part of the flexible membrane is separated from a second overlapping part of the flexible membrane by an external wall of the elongate main body.

14. An electrosurgical instrument according to claim 1, wherein the housing is a non-telescopic housing.

15. An electrosurgical instrument according to claim 1, wherein the grippable member is connected to the middle portion of the elongate main body such that an axial position of the grippable member relative to the elongate main body is configured to be adjusted in use, the front and rear portions extending circumferentially around outer surfaces of the middle portion to form stops for the grippable member.

* * * * *